United States Patent [19]
Hubl et al.

[11] Patent Number: 5,162,351
[45] Date of Patent: Nov. 10, 1992

[54] BENZOISOTHIAZOLES, THEIR PREPARATION AND THEIR USE AS PESTICIDES

[75] Inventors: Dieter Hubl, Bergkamen; Ernst Pieroh, Berlin, both of Fed. Rep. of Germany

[73] Assignee: Schering Aktiengesellschaft, Fed. Rep. of Germany

[21] Appl. No.: 431,643

[22] Filed: Nov. 3, 1989

[30] Foreign Application Priority Data

Nov. 3, 1988 [DE] Fed. Rep. of Germany ....... 3837578

[51] Int. Cl.⁵ .................... C07D 417/00; A61K 31/41
[52] U.S. Cl. ........................................ 514/372; 548/209
[58] Field of Search ........................ 548/209; 514/372

[56] References Cited

U.S. PATENT DOCUMENTS

| | | | |
|---|---|---|---|
| 3,627,776 | 3/1969 | Bosmagen | 548/209 |
| 3,707,364 | 12/1972 | Beche | 548/209 |
| 4,871,754 | 10/1989 | Bauer et al. | 514/273 |

FOREIGN PATENT DOCUMENTS

| | | |
|---|---|---|
| 3202298 | 8/1983 | Fed. Rep. of Germany . |
| 48-13543 | 2/1973 | Japan . |
| 1113634 | 5/1968 | United Kingdom . |

*Primary Examiner*—Nicholas S. Rizzo
*Attorney, Agent, or Firm*—Ostrolenk, Faber, Gerb & Soffen

[57] ABSTRACT

There are described new benzoisothiazoles of general formula I

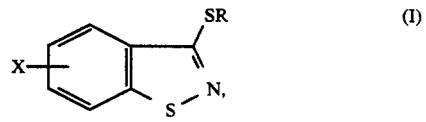

wherein X and R have meanings given in the description, a process for their preparation and their use as pesticides, especially against nematodes.

10 Claims, No Drawings

BENZOISOTHIAZOLES, THEIR PREPARATION AND THEIR USE AS PESTICIDES

This invention relates to new benzoisothiazoles, their preparation as well as their use as pesticides, especially against nematodes.

3-Thio-5-nitrobenzoisothiazoles are known which possess strong bacterial and fungicidal properties (DE 3 202 298).

The object of the present invention is to provide pesticides with better properties.

It has now been found that compounds of general formula I

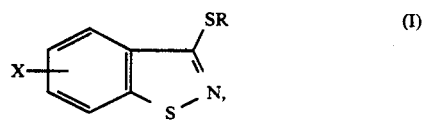

wherein

X is hydrogen, halogen, $C_{1-4}$-alkyl, $C_{1-4}$-alkylthio, $C_{1-4}$-alkoxy, di-$C_{1-4}$-alkylamino, halo-$C_{1-4}$-alkyl, halo-$C_{1-4}$-alkoxy, halo-$C_{1-4}$-alkylthio, $C_{3-6}$-cycloalkyl, halo-$C_{3-6}$-cycloalkyl, halo-$C_{3-6}$-cycloalkylmethoxy, halo-$C_{3-6}$-cycloalkyl-methylthio, nitro, cyano, amino, phenyl, halophenyl, phenoxy, phenylthio or halophenylthio groups, and R is $C_{1-12}$-alkyl, $C_{2-12}$-alkenyl, $C_{2-12}$-alkynyl, $C_{3-6}$-cycloalkyl or $C_{3-6}$-cycloalkylmethyl, each of which is optionally substituted, one or more times by the same or different halogen, show a surprisingly good nematicidal activity coupled with good plant compatibility.

By the term "halogen" is to be understood Cl, F, Br and iodine. The term haloalkyl, haloalkoxy, haloalkylthio and halocycloalkyl means that one or more hydrogen atoms of the alkyl or cycloalkyl group, respectively, are replaced by halogen.

The compounds of the invention of general formula I can be prepared according to known methods by reacting compounds of general formula II,

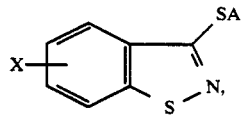

in which X has the meaning given above and A is hydrogen, ammonium or an alkali metal, is reacted with a compound of formula Z-R, in which Z is a leaving group, such as for example halogen, mesylate and tosylate, and R has the meaning given in formula I, in an inert solvent or solvent mixture, preferably at raised temperature and preferably at raised pressure, in the presence of a base.

Suitable bases include organic and inorganic bases, such as for example tertiary amines, e.g. triethylamine or tripropylamine, alkali metal and alkaline earth metal hydrides, hydroxides, carbonates and bicarbonates and also alkali metal alcoholates, such as sodium methylate or potassium tert.-butylate.

Suitable solvents for the preparation of the compounds of the invention include for example diethyl ether, dioxane and tetrahydrofuran; aliphatic and aromatic hydrocarbons, such as toluene and petroleum ether; halogenated hydrocarbons, e.g. chlorobenzene, methylene chloride, carbon tetrachloride and chloroform, nitriles such as acetonitrile and propionitrile; N,N-dialkylamides, such as for example dimethylformamide; ketones, such as acetone and methyl ethyl ketone; dimethyl sulphoxide, sulpholane, as well as water and alcohols, e.g. methanol, ethanol, isopropanol or butanol, and mixtures of such solvents.

The temperature of the reaction depends on the reactants and can vary between $-70°$ C. and $120°$ C. The pressure also depends on the reactants and can lie between 1 and 25 bar. The reaction usually lasts from ca. 0.5 to 48 hours. The reaction mixture can be poured into ice/water, extracted and worked up in known manner. The resulting products can be purified in conventional manner, for example by recrystallisation, vacuum distillation or column chromatography.

The compounds of formula II used as starting material are either known or can be obtained in an analogous way to known processes.

Because of the nematicidal activity coupled with good plant compatibility, the compound according to the invention can be successfully applied in plant protection as pesticides in agriculture, in vine and fruit growing, in horticulture and in forestry.

Plant parasitic nematodes which can be controlled according to the invention include for example root-knot nematodes, such as *Meloidogyne incognita, Meloidogyne hapla* and *Meloidogyne javanica*, cyst forming nematodes, such as *Globodera rostochiensis, Heterodera schacktii, Heterodera avanae, Heterodera glycines* and *Heterodera trifolii*, and stem and leaf eelworms, such as *Ditylenchus dipsaci, Ditylenchus destructor, Aphelenchoides ritzemabosi, Pratylenchus neglectus, Pratylenchus penetrans, Pratylenchus curvitatus*, as well as *Tylenchorhynchus dubius, Tylenchorhynchus claytoni, Rotylenchus robustus, Heliocotylenchus multicinctus, Radopholus similis, Belonolaimus longicaudatus, Longidorus elongatus* and *Trichodorus primitivus*.

Based on their insecticidal and acaricidal properties, the compounds of the invention further offer the possibility of treatments against pests in the different stages of crops as well as human and animal pests.

The use of the active ingredients of the invention can be carried out in the form of their conventional commercial formulations and/or the ready to use preparations from these formulations.

The content of active ingredient in the ready to use preparations obtained from the commercial concentrated formulations can vary over wide ranges. The rate of use for the control of nematodes lies between 0.003 kg to around 10 kg per hectare, preferably from around 0.3 kg to around 6 kg per hectare.

The active ingredient or their mixtures can be applied in the usual formulations such as solutions, emulsions, wettable powders, suspensions, powders, dusts, foams, pastes, soluble powders, granules, aerosols, suspension concentrates, seed dressings, natural and synthetic substances impregnated with the active ingredients, microcapsules in polymers and in seed coatings for seeds, as well as formulations with burning substances such as smoke cartridges, smoke capsules and smoke spirals amongst others as well as ULV-cold and hot fogging formulations.

These formulations can be prepared in known manner for example by mixing the active ingredient with diluents such as liquid solvents, and liquefied gases and-/or solid carriers, optionally using surface active agents such as emulsifiers and/or dispersing agents and/or foaming agents.

When using water as the diluent, organic solvents can also be used for example as auxiliary solvents.

Examples of liquid solvents include aromatic hydrocarbons, such as xylene, toluene or alkynaphthalenes, chlorinated aromatic or chlorinated aliphatic hydrocarbons, such as chlorobenzene, chloroethylene or methylene dichloride, aliphatic hydrocarbons, such as cyclohexane or paraffins, for example mineral oil fractions, alcohols, such as butanol and glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

By the term liquefied gaseous diluents or carriers are meant those substances which are gaseous at normal temperature and pressure, for example aerosol blowing agents, such as halohydrocarbons, as well as butane, propane, nitrogen and carbon dioxide.

Examples of solid carriers are natural earth powders, such as kaolin, alumina, talc, chalk, quartz, attapulgite, montmorillonite or diatomaceous earths and synthetic powders, such as finely divided silica, aluminium oxide and silicates as well as solid carriers for granules, crushed and fractionated natural rocks, such as calcite, marble, pumice, sepiolith and dolomite, as well as synthetic granules from inorganic and organic powders as well as granules from organic materials such as sawdust, coconut shells, maize cobs and tobacco stalks.

Examples of emulsifying and/or foaming agents include non-ionic and anionic emulsifiers, such as polyoxyethylene-fatty acid esters, polyoxyethylene-fatty alcohol ethers, for example alkylaryl-polyglycol-ethers, alkylsulphonates and arylsulphonates as well as protein hydrolysates.

Dispersing agents include for example lignin, sulphite waste liquors and methylcellulose.

There can also be used in the formulations sticking agents such as carboxymethylcellulose, natural and synthetic powdery, granulated or latex-forming polymers, as well as gum arabic, polyvinyl alcohol and polyvinyl acetate.

There can also be used dyestuffs, such as inorganic pigments, for example iron oxide, titanium oxide, ferrocyan blue and organic dyestuffs such as alizarin- and azo-metal phthalocyanine dyestuffs and trace elements such as salts of iron, manganese, boron, copper, cobalt, molybdenum and zinc.

The formulations contain in general between 0.1 and 95 weight percent of the active ingredient, preferably between 0.5 and 90 percent.

Examples of formulations are:

I. Wettable powder 10 parts by weight of the compound of Example 1 were intimately mixed with 12 parts by weight of calcium lignosulphonate, 76 parts by weight of finely divided kaolin and 2 parts by weight of dialkylnaphthalene sulphonate and then milled.

II. Dusting powder 2.5 parts by weight of the compound of Example 1 were dissolved in 10 methylene chloride and added to a mixture of 25 parts by weight of finely divided silicic acid and 71.5 parts by weight talc and 1 part by weight sudan red. The solvent was removed in vacuo and the residue finely milled.

III. Granule 5 parts by weight of the weight of the compound of Example 1 were dissolved in 10 parts by weight of methylene chloride and sprayed onto 95 parts by weight granulated attapulgite of particle size 0.3–0.8 mm and dried.

IV. Emulsifiable concentrate 20 parts by weight of the compound of Example 1 were dissolved in a mixture of 75 parts by weight of isophorone and 5 parts by weight of a mixture of 30 parts by weight of calcium benzene sulphonate and 30 parts by weight of castor oil polyglycolate with 40 mole % ethylene oxide and 40 parts by weight of a copolymer of propylene- and ethylene oxide.

The following Examples illustrate the preparation of compounds of the invention.

EXAMPLE 1

3-Difluoromethylthio-1,2-benzoisothiazole 4.1 g (0.02 mol) Potassium 1,2-benzoisothiazole-3-thiolate was suspended in 25 ml dioxane and treated with a solution of 5.6 g (0.10 mol) potassium hydroxide in 9 ml water. At a temperature of 60°–70° C., a slow stream of chlorodifluoromethane was passed through over 30 minutes. The mixture was added to 500 ml ice/water and extracted several times with ethyl acetate. The organic phase was dried over magnesium sulphate, filtered and concentrated. The residual oil was purified by silica gel column chromatography (eluent: hexane/diethyl ether 9:1).

Yield: 1.0 g=22.9% of theory.
$n_D^{20}$: 1.59912.

EXAMPLE 2

3-(3,4,4-Trifluoro-3-butenylthio)-1,2-benzoisothiazole 2.05 g (0.01 mol) Potassium 1,2-benzoisothiazole-3-thiolate was suspended in 25 ml dimethylformamide. At a temperature of 20° C., a solution of 2.3 g (0.01 mol) 4-bromo-1,1,2-trifluorobut-1-ene in 10 ml dimethylformamide was added dropwise. The mixture was then stirred for 2 hours at room temperature. The mixture was added to 300 ml ice/water and extracted several times with ethyl acetate. The organic phase was dried over magnesium sulphate, filtered and concentrated. The residual oil was purified by silica gel column chromatography (eluent: hexane/diethyl ether 9:1).

Yield: 0.60 g=22% of theory.
$n_D^{20}$: 1.58008.

In a similar manner, the following compounds of formula I were prepared.

| Example No | X | R | $n_D^{20}$/mp(°C.) |
|---|---|---|---|
| 3 | H | —CF$_2$CF$_2$Br | 1,56868 |
| 4 | H | —CH$_2$—CH(CF=CF$_2$) | 1,59688 |
| 5 | H | —CF$_2$Br | 1,62668 |
| 6 | H | —CH$_2$CH$_2$F | 1,62330 |
| 7 | 5-NO$_2$ | —CHF$_2$ | 74–76 |
| 8 | 5-NO$_2$ | —CH$_2$CH$_2$CF=CF$_2$ | 69–71 |
| 9 | 6-Cl | —CH$_2$CH$_2$CF=CF$_2$ | 1,60740 |

-continued

| Example No | X | R | $n_D^{20}$/mp(°C.) |
|---|---|---|---|
| 10 | 6-F | —CH$_2$CH$_2$CF=CF$_2$ | 1,54716 |
| 11 | 6-CF$_3$ | —CH$_2$CH$_2$CF=CF$_2$ | 1,53282 |
| 12 | 5-NO$_2$ | —CF$_2$Br | 74–76 |

The following use examples illustrate the biological activity of the compounds of the invention.

USE EXAMPLE A

Control of root knot nematode, *Meloidogyne incognita*.

10% of a powder preparation of the active ingredient was mixed thoroughly with soil that had been strongly infested with the test nematode. After this the treated soil was put into a 0.5 liter fermenting tube, treated with cucumber seeds and cultivated at a soil temperature of 25° to 27° C. in a greenhouse. After a cultivation time of 25 to 28 days the cucumber roots were washed and inspected in a water bath for nematode attack (root knots) and the % level of activity of the active ingredients compared with a treated control was determined. When the nematode attack is fully controlled the level of activity is 100%.

At a dose of 10 mg or less of active substance per liter of soil, a nematode attack by *Meloidogyne incognita* was fully controlled (100%) by the compound of Example 2.

USE EXAMPLE B

Activity in the prophylactic treatment of feed against the two spotted mite (*Tetranychus urticae* Koch)

From the developed primary leaf of field beans (*Phaseolus vulgaris* nanus Aschers.) 14 mm diameter discs were cut. Some of these were treated with a 0.1% aqueous preparations of compounds of the invention and these together with untreated discs were placed on filter papers with the underside of the leaves turned upwards. After drying the test pieces, they were each infested with six adult female *Tetranychus urticae* and maintained for 3 days at 25° C. and 16 hours light per day. The experiment was replicated 4 times. Dead and alive adults were then counted and removed. Similarly the number of eggs laid were counted. After a further 7 days, the number of living larvae were counted, the activity calculated using Abbott's method in comparison with the untreated controls.

The compounds of the invention of Examples 2 and 5 showed 80–100% activity.

USE EXAMPLE C

Activity in the curative treatment against eggs of the two spotted mite (*Tetranychus urticae* Koch)

From the developed primary leaf of field beans (*Phaseolus vulgaris* nanus Aschers.) 14 mm diameter discs were cut and laid with the upper surface face down on wet filter paper. Each disc was infested with at least 5 adult female *Tetranychus urticae* and maintained for 2 days at around 25° C., 50–60% relative humidity and 16 hours light per day. After collecting the adults, the leaf discs with the laid eggs were dipped in a preparation containing 0.016% of active ingredient and surfactant. As a control, leaf discs were dipped in water containing surfactant in the same concentration as in the preparations containing active ingredient. After counting the eggs, the leaf discs were maintained for 7 days at around 25° C., 50–60% relative humidity and 16 hours light per day. From the percentage difference of laid eggs and living larvae in comparison with the controls, the activity was calculated using Abbott's method. The average of three replicates was recorded.

An activity of 80% or more was shown by the compound of the invention of Example 4.

USE EXAMPLE D

Activity against eggs/larvae of the corn rootworm (*Diabrotica undecimpunctata*)

Formulations of compounds of the invention were made up as aqueous emulsions at a concentration of 0.1%. 0.2 ml of these preparations were pipetted onto soil in polystyrene petri dishes each of which contained 1 maize seedling and in the center of the dish about 50 eggs of the corn rootworm (*Diabrotica undecimpunctata*). The closed pots were left at 25° C. under extended daylight conditions for 4 days. The criterion for judging the activity was the mortality eggs or the newly emerged larvae.

The compound of Example 5 showed 80–100% activity.

We claim:

1. Compounds of formula I

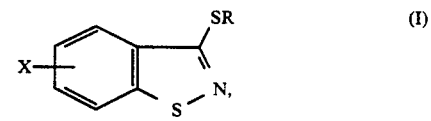

wherein

X is hydrogen, halogen, C$_{1-4}$-alkyl, di-C$_{1-4}$-alkylamino, halo-C$_{1-4}$-alkyl, halo-C$_{1-4}$-alkoxy, halo-C$_{1-4}$-alkylthio, C$_{3-6}$-cycloalkyl, halo-C$_{3-6}$-cycloalkyl, halo-C$_{3-6}$-cycloalkylmethoxy, C$_{3-6}$-cycloalkylmethylthio, cyano, amino, phenyl, halophenyl, phenoxy, phenylthio or halophenylthio groups, and R is C$_{1-12}$-alkyl, C$_{2-12}$-alkenyl, C$_{2-12}$-alkynyl, C$_{3-6}$-cycloalkyl or C$_{3-6}$-cycloalkylmethyl, each of which is optionally substituted, one or more times by the same or different halogen.

2. A pesticidal composition which comprises a compound according to claim 1 in admixture with agriculturally acceptable diluents or carriers.

3. Compound according to claim 1 wherein X is hydrogen, halogen or halo-C$_{1-4}$-alkyl and R is halo-C$_{1-12}$-alkyl, halo-C$_{2-12}$-alkenyl or halo-C$_{3-6}$-cycloalkylmethyl.

4. Compound according to claim 3 in which X is hydrogen, fluorine, chlorine or trifluoromethyl and R is C$_{1-4}$-alkyl substituted by fluoro or bromo, fluoro substituted butenyl or fluoro substituted cyclopropylmethyl.

5. Compound according to claim 4 in which X is hydrogen.

6. Compound according to claim 5 in which R is bromodifluoromethyl, trifluorobutenyl or difluorocyclopropylmethyl.

7. A nematocidal composition which comprises a compound according to claim 3 in admixture with agriculturally acceptable diluents or carriers.

8. A nematocidal composition which comprises a compound according to claim 4 in admixture with agriculturally acceptable diluents or carriers.

9. A nematocidal composition which comprises a compound according to claim 5 in admixture with agriculturally acceptable diluents or carriers.

10. A nematocidal composition which comprises a compound according to claim 6 in admixture with agriculturally acceptable diluents or carriers.

* * * * *